United States Patent [19]

Ou

[11] Patent Number: 5,167,797
[45] Date of Patent: Dec. 1, 1992

[54] REMOVAL OF SULFUR CONTAMINANTS FROM HYDROCARBONS USING N-HALOGENO COMPOUNDS

[75] Inventor: John D. Y. Ou, Houston, Tex.

[73] Assignee: Exxon Chemical Company Inc., Linden, N.J.

[21] Appl. No.: 624,001

[22] Filed: Dec. 7, 1990

[51] Int. Cl.$^5$ .............................. C10G 29/20
[52] U.S. Cl. .................. 208/236; 208/237; 208/240; 208/241; 208/301; 585/860; 585/862
[58] Field of Search .............. 208/207, 226, 229, 230, 208/236, 237, 241, 240, 301; 585/860, 862

[56] References Cited

U.S. PATENT DOCUMENTS

| | | | |
|---|---|---|---|
| 1,783,901 | 12/1930 | Bottoms | 423/574 |
| 3,306,945 | 2/1967 | Conviser | 208/310 |
| 3,367,862 | 2/1968 | Mason et al. | 208/247 |
| 3,756,976 | 9/1973 | Uraneck et al. | 521/82 |
| 3,898,153 | 8/1975 | Louder et al. | 208/89 |
| 3,945,914 | 3/1976 | Yoo et al. | 208/240 |
| 4,035,474 | 7/1977 | Kunkel et al. | 423/574 |
| 4,225,417 | 9/1980 | Nelson | 208/89 |
| 4,283,373 | 8/1981 | Frech et al. | 423/226 |
| 4,320,220 | 3/1982 | Pampouchidis | 524/591 |
| 4,456,527 | 6/1984 | Buss et al. | 208/89 |
| 4,534,943 | 8/1985 | Novak et al. | 422/188 |
| 4,575,415 | 3/1986 | Novak et al. | 208/91 |
| 4,592,892 | 6/1986 | Ueno et al. | 422/28 |
| 4,634,518 | 1/1987 | Buss et al. | 208/138 |

FOREIGN PATENT DOCUMENTS

| | | |
|---|---|---|
| 0074894 | 3/1983 | European Pat. Off. . |
| 3527110 | 2/1986 | Fed. Rep. of Germany . |
| 2209386 | 5/1989 | United Kingdom . |

OTHER PUBLICATIONS

Talanta, The International Journal of Pure and Applied Analytical Chemistry, Jan.-Dec., vol. 22, 1975.
Tsujihara et al., Sulfilimine I. Synthesis and Formation Mechanism, Bulletin of Chemical Society in Japan, vol. 42, 2631–2635(1969).
McCall et al., The Hydrogenolysis of Sulfilimines and its Application to the Purification of Sulfides, vol. 73, Sep. 1951, pp. 4476–4478.

Primary Examiner—Theodore Morris
Assistant Examiner—William C. Diemler
Attorney, Agent, or Firm—Edward F. Sherer

[57] ABSTRACT

The present invention is directed to a process for removal of sulfur contaminants from hydrocarbons using processes which rely upon the reaction of organosulfur compounds with N-halogeno compounds. The sulfur removal may be effected by using liquid/liquid extraction processes or one of two reactive adsorption processes involving injecting a stoichiometric amount of N-halogeno compounds into hydrocarbon and then passing the stream through an adsorbent column to adsorb the N-halogeno-sulfur compounds and any unreacted N-halogeno compounds; or using adsorbents which are pre-loaded with N-halogeno compounds which are placed in a fixed-bed column for sulfur removal.

24 Claims, 2 Drawing Sheets

REMOVAL OF SULFUR CONTAMINANTS FROM HYDROCARBONS USING N-HALOGENO COMPOUNDS

1. FIELD OF THE INVENTION

The present invention relates to the removal of sulfur compounds from streams. More particularly, the present invention relates to the removal of organosulfur compounds, such as mercaptans, sulfides and disulfides, from liquid hydrocarbon streams. Specifically, the present invention is directed to the removal of organosulfur compounds from hydrocarbons by reactive extraction, as well as removing organosulfur compounds from hydrocarbon streams by reactive adsorption.

2. DISCUSSION OF BACKGROUND AND MATERIAL INFORMATION

The removal of sulfur compounds and particularly chemically-combined sulfur, such as organosulfur compounds, from feedstreams is highly desirable for environmental concerns and in order to prevent potential catalyst deactivation as well as equipment corrosion.

Typically, hydrocarbon products contain various amounts of sulfur compounds in the form of, for example, chemically-combined sulfur, such as inorganically combined sulfur and organically combined sulfur, i.e., organosulfur compounds.

The presence of organosulfur compounds in hydrocarbon streams results naturally, as well as from the introduction of organosulfur compounds, into the hydrocarbon streams during conventional processes for producing and treating hydrocarbon products.

As previously indicated, if chemically-combined sulfur, such as organosulfur compounds, are not removed from the hydrocarbon streams, the presence of organosulfur compounds in the resultant hydrocarbon products, including natural gas, paraffins, olefins and aromatics, particularly gasoline or other fuels, can cause corrosion of processing equipment and engine parts, as well as other deleterious effects, particularly when water is present.

U.S. Pat. No. 4,283,373, FRECH et al., is directed to a method of removing sulfur compounds from a gas stream by contacting the stream with alkali metal salts of sulfonamides. The preferred sulfonamide disclosed is chloramine-T which can be sprayed into the gas stream, or the gas can be passed through a porous carrier impregnated with the chloramine, or through a resin with pendant substituted sulfonamide groups.

The information disclosed by FRECH et al. as background for sulfur removal include the following:

U.S. Pat. No. 1,783,901 relates to removing $H_2S$ from natural gas depending upon the reactivity of the $H_2S$ with amino nitrogen.

U.S. Pat. No. 4,035,474, KUNKEL et al., is directed to a method for removal of sulfur from tail gas by use of a cold bed absorption process which utilizes a catalyst.

U.S. Pat. No. 3,756,976, URANECK et al., removes thiol odor from polymer latex through the use of numerous compounds that convert odiferous sulfur compounds to non-odiferous form, i.e., the use of alkali metal salts of N-halogenated arylsulfonamides.

U.S. Pat. No. 3,306,945, CONVISER, is directed to a process for purifying liquid unsaturated hydrocarbons of by removing impurities using molecular sieve materials. CONVISER discloses that sulfides (R—S—R), which include dialkyl sulfides, may be adsorbed by zeolitic molecular sieves material having sufficiently large pores to such impurities, such as the synthetic type X.

U.S. Pat. No. 4,592,892, EBERLY, Jr., is directed to a process of using a sorbent catalyst to remove sulfur from naphtha. The sulfur impurities which are disclosed as being removed are mercaptans, thiophenes, disulfides, thioethers, hydrogen sulfide, carbonyl sulfide, and the like; and the adsorbent is disclosed as a Group VI B and/or Group VIII metal catalyst, for example, cobalt molybdate or nickel molybdate supported on alumina.

U.S. Pat. No. 3,367,862, MASON et al., is directed to a process for desulphurizing heavy residual fractions by contacting with water in the presence of the catalyst comprising the metal, metal oxide, or metal sulfide, distended on a charred base.

Naphthas, which are used for reforming, typically contain between 50 wppm to 500 wppm sulfur as mercaptans, such as 2-propyl mercaptan, butyl mercaptan, and thiophene, hindered thiophenes, such as 2, 5-dimethylthiophene. Accordingly, naphthas for reforming are usually treated with hydrogen over a hydrotreating catalyst, such as a sulfided cobalt and molybdenum on alumina support, or nickel and molybdenum on alumina support, to protect reforming catalysts. Hydrotreating converts sulfur compounds to hydrogen sulfide, decomposes nitrogen and oxygen compounds and saturates olefins. Hydrotreating is done at a temperature between about 400° F. and 900° F., a pressure between 200 psig and 750 psig, liquid hourly space velocity between 1 and 5, and hydrogen circulation rate of 500 to 3000 scf/hr. Modern hydrotreating processes can reduce sulfur concentration in naphtha to 0.25 wppm and even to 0.1 wppm.

U.S. Pat. No. 3,898,153 is directed to purifying reformer feedstreams by passing hydrotreated reformer feedstock through a zinc oxide bed.

U.S. Pat. No. 4,634,518 passes hydrotreated reformer feed over massive nickel catalysts.

Other treatments for purifying hydrotreated feedstock for reforming are disclosed in U.S. Pat. Nos. 4,320,220; 4,225,417; 4,575,415; and 4,534,943; wherein the disclosed treatment is over manganese oxides.

A suitable manganese oxide formulation for this purpose which is commercially available is Sulfur Guard HRD-264 sold by Englehard wherein recommended treatment conditions are temperatures within the range of 600° F. to 1000° F., pressures within the range of about 150 psig to 700 psig, 1/1 to 30/1 hydrogen to oil molar ratio, and 500 to 50,000 ghsv.

U.S. Pat. No. 4,456,527 is directed to purifying hydrotreated feed for reforming over zeolite L catalysts.

German Patent No. 3 527 110-A, CIBA GEIGY AG, is directed to removing hydrogen sulfide from gases by oxidation using a solution containing anthraquinone sulphonamide and variable valency metal compounds followed by reoxidation, preferably using oxygen of hydroquinone.

The process is disclosed as being useful to purify gas, town gas, waste gases, and $CO_2$ rich streams from coal combustion, wherein the impurities which may be present are identified as including certain oxides of C, N and S, $H_2$, organic S compounds, and HCN.

British Patent No. 2 209 386, CIBA GEIGY AG, is directed to the removal of hydrogen sulphide from gases or liquid hydrocarbons by washing with alkaline solution containing anthraquinone disulphonamides. It is disclosed that hydrogen sulfide in gases is adsorbed, for subsequent removal in sulfur, by washing the gas with an aqueous alkaline solution of one or more anthraquinone sulphonamides.

European Application No. 74 894, CIE FRANCAISE RAFFINAGE, is directed to the extraction of hydrogen sulfide, carbon dioxide and the like, from hydrocarbon gases using sulphonamide or sulphamide as solvent. It is disclosed that undesirable gases, for example, $H_2S$, $CO_2$, COS, and mercaptans, are removed from their mixtures with hydrocarbons and/or $H_2$ by a solvent whose molecule contains at least one group $N-SO_2$, and preferably a sulphonamide or sulphamide.

SUMMARY OF THE PRESENT INVENTION

In general, the present invention relates to removing organosulfur compounds from liquid hydrocarbons. More specifically, the present invention is based on the discovery that the effectiveness of sulfur removal from liquid hydrocarbon streams is improved by using a technique selected from the group consisting of reactive extraction, reactive adsorption, and adsorption using adsorbents pre-loaded with N-halogeno compounds.

In accordance with the present invention, it has been discovered that N-halogeno compounds are capable of removing mercaptans, sulfides and disulfides, even from streams containing high levels of polyolefins, such as diolefins.

For purposes of the present invention, the sulfur removal techniques are based on the spontaneous chemical reactions between N-halogeno compounds such as chloramine-T or chloramine-B, and organosulfur compounds.

In one of the reactive extraction embodiments of the present invention, the sulfur compound removal may be accomplished using a liquid/liquid process because it has been discovered that some of the N-halogeno compounds and their reaction products of N-halogeno-sulfur compounds are more soluble in water, than in paraffins, olefins or aromatics.

In a particularly preferred embodiment, one can use an aqueous solution of these N-halogeno compounds to react with the sulfur compounds, and extract the reaction products from the hydrocarbon phase to the aqueous phase.

In one of the reactive adsorption processes, referred to herein as Adsorption Process I, a stoichiometric amount of N-halogeno compounds may be injected into the hydrocarbon stream. Subsequently, the resultant stream is passed through an adsorbent column to adsorb the N-hologeno-sulfur compounds and any unreacted N-halogeno compounds.

In the second reaction adsorption process, i.e., Adsorption Process II, adsorbents which are pre-loaded with N-halogeno compounds are used to effect the sulfur removal. For purposes of this embodiment, adsorbents are prepared by saturating porous supports, such as activated carbons and zeolites, with an aqueous solution of N-halogeno compounds. The N-halogeno compounds-loaded adsorbents may then be placed in conventional fixed-bed columns for sulfur removal.

Preferred adsorbents and porous supports suitable for purposes of these embodiments of the present invention include zeolites, activated carbon, clay, alumina, silicate gel and like adsorbents.

DETAILED DESCRIPTION OF THE INVENTION

Figure 1:
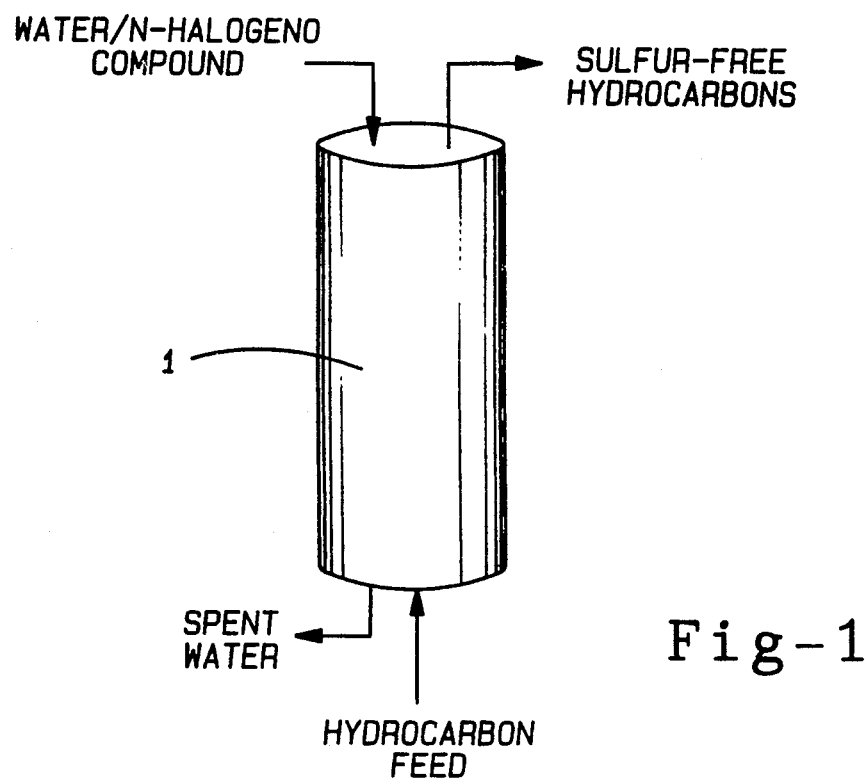
FIG. 1 is an illustration of a counter current continuous reactive extraction process for sulfur removal.

The present invention involves removing chemically-combined sulfur, such as organosulfur compounds, from liquid hydrocarbon streams containing organosulfur compounds, by contacting the hydrocarbon stream containing organosulfur compounds with appropriate materials containing N-halogeno compounds for a time and under conditions sufficient for the organosulfur compounds to react with N-halogeno compounds to produce N-halogeno-sulfur compounds as reaction products.

N-halogeno compounds suitable for purposes of the present invention include those having the following general formulae:

$$R_1SO_2NXM \quad (I)$$

wherein $R_1$ is a member selected from the group consisting of Ph, $PhCH_2$, p—$CH_3C_6H_4$, p—$ClC_6H_4$, p—$BrC_6H_4$, p—$NO_2C_6H_4$, p—$CH_3CONHC_6H_4$, p—$NH_2C_6H_4$, p—$PhN=NC_6H_4$, 2-Thienyl, and $(CH_3)_m(CH_2)_n$, where m and n are integers equal to or greater than zero; X is a radical selected from the group consisting of chlorine, bromine, and iodine radicals; and M is a radical selected from the group consisting of hydrogen, lithium, sodium, and potassium radicals.

$$R_2CONXM \quad (II)$$

wherein $R_2$ is a member selected from the group consisting of $CH_2Cl$, $CHCl_2$, $CHBr_2$, $NH_2$, Ph, p—$CH_3OC_6H_4$, $(CH_3)_m(CH_2)_n$, and $(CH_3)_m(CH_2)_nO$, wherein m and n are integers equal to or greater than zero; X is a radical selected from the group consisting of chlorine, bromine, and iodine radicals; and M is a radical selected from the group consisting of hydrogen, lithium, sodium, and potassium radicals.

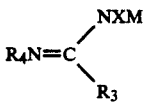

$$R_4N=C\begin{matrix}NXM\\ \\R_3\end{matrix} \quad (III)$$

wherein $R_3$ is a member selected from the group consisting of $CH_3$ and Ph; and wherein $R_4$ is a member selected from the group consisting of H, $NH_2$, $N(CH_3)_2$, $(CH_2)_3$, Ph, $PhCl_2$, p—$CH_3C_6H_4$, o—$CH_3C_6H_4$, p—$ClC_6H_4$, o—$ClC_6H_4$, and 2-Pyridyl; X is a radical selected from the group consisting of chlorine, bromine, and iodine radicals; and M is a radical selected from the group consisting of hydrogen, lithium, sodium, and potassium radicals.

$$C_4H_4O_2NX \quad (IV)$$

wherein X is a radical selected from the group consisting of chlorine, bromine, and iodine radicals.

Preferred for reactive extraction processes, Adsorption Process I, and Adsorption Process II, are N-halogeno compounds which are water soluble but not soluble in organic solvents, such as those selected from the group consisting of N-halogeno-N-metalloarylsulfonamidates and N-halogeno-N-metalloalkylsulfonamidates, i.e., chloramine-T and chloramine B, which are more preferred for use with adsorption process II and most preferred for use with reactive extraction processes. N-halogeno compounds which are soluble in organic solvents, such as N-chlorosuccinimide, are preferred for purposes of adsorption process I.

Other N-halogeno compounds suitable for purposes of the present invention are N-halogeno compounds derived from a member selected from the group consisting of amides, amidines, guanidines, urea, urethane, and succinimide, i.e., N-halogeno-N-metallocarbamates, and N-chlorosuccininide.

The present invention is also directed to removing organosulfur compounds from a hydrocarbon stream containing olefinic compounds, paraffins, and aromatics and organosulfur compounds by contacting the hydrocarbon stream with a suitable adsorbent for removing N-halogeno sulfur compounds for a time and under conditions suitable for permitting the reaction of organosulfur compounds and N-halogeno compounds to occur.

In one embodiment, the removal may be accomplished using a liquid/liquid extraction process due to the fact that some N-halogeno compounds and the reaction products of N-halogeno-sulfur compounds are more soluble in water than in paraffins, olefins or aromatics.

In another embodiment, a stoichiometric amount of N-halogeno compounds is injected into the hydrocarbon stream and the resultant stream is passed through an adsorbent column to adsorb the N-halogeno-sulfur compounds and any unreacted N-halogeno compounds.

In yet another preferred embodiment, the sulfur removal is accomplished using adsorbents which are preloaded with N-halogeno compounds. In this embodiment, the adsorbents are prepared by saturating porous supports, such as activated carbon and zeolites, with N-halogeno compounds and placing the N-halogeno compound-loaded adsorbents in conventional fixed-bed columns for sulfur removal.

As indicated above, adsorbents or porous supports, suitable for purposes of the present invention, include zeolites, activated carbons, clay, alumina, silicate gel and other molecular sieves.

For purposes of the present invention, molecular sieves having an effective pore size of from more than about 5 Angstrom units to about 15 Angstrom units are suitable; however, molecular sieves having an effective pore size within the range of about 7 Angstrom units to about 10 Angstrom units are preferred, with molecular sieves having an effective pore size within the range of about 10 Angstrom units being more preferred.

The zeolite preferred for purposes of the present invention has a pore size within the range of about more than 5 Angstrom units to about 15 Angstrom units, and may be in the form of crushed or beaded particles. For purposes of the present invention include zeolite X, Y, beta and mordenite are the more preferred zeolites. However, zeolite X, i.e., sodium X zeolite, is the most preferred zeolite. Zeolite X molecular sieves are described in U.S. Pat. No. 2,883,244, a specific example which is disclosed in U.S. Pat. No. 3,862,900, the disclosures of which are hereby incorporated by reference herein thereto.

Properties of zeolites suitable for this application are described, for example, in "Zeolite Molecular Sieves" by D. W. Breck, R. E. Krieger Publishing Co., 1984. The zeolites are commercially available from UOP Inc. Properties of some zeolites are listed below:

| Zeolite X | |
|---|---|
| Average composition: | $Na_2O.Al_2O_3.2,5SiO_2.6H_2O$ |
| Pore Diameter: | ~10 A |
| Reference: | R. M. Milton, U.S. Pat. No. 2,882,244 (1959) |

| Zeolite Y | |
|---|---|
| Average composition: | $Na_2O.Al_2O_3.4.8SiO_2.8.9H_2O$ |
| Pore Diameter: | ~10 A |
| Reference: | D. W. Breck, U.S. Pat. No. 3,130,007 (1964) |

| Zeolite Mordenite | |
|---|---|
| Average composition: | $Na_2O.Al_2O_3.9-10SiO_2.6H_2O$ |
| Pore Diameter: | ~7 A |
| Reference: | R. M. Milton, U.S. Pat. No. 2,882,244 (1959) |

Alumina suitable for purposes of the present invention may be selected from conventional alumina adsorbents which have appropriate high adsorptive power, a high surface area, suitable hardness, resistance to crumbling during handling and use, suitable size and granular form. A representative example of alumina suitable for purposes of the present invention is disclosed in U.S. Pat. No. 3,864,243, the disclosure of which is hereby incorporated by reference herein thereto. The following description relates to alumina suitable for purposes of the present invention.

| Kaiser Activated Alumina A-201 (neutral) 8 × 14 mesh spheres with a high surface area (325 $m^2/gm$) | |
|---|---|
| Typical analysis (dry basis) | 93.25% $Al_2O_3$ |
| | 0.35% $Na_2O$ |
| | 0.02% $Fe_2O_3$ |
| | 0.02% $SiO_2$ |

The liquid hydrocarbon stream including the organosulfur compounds treated in accordance with the present invention preferably includes paraffins, aromatics and olefin compounds. The olefinic compounds present in the hydrocarbon stream are selected from the group consisting of mono-olefins, polyolefins, linear olefins, branched olefins, alpha olefins and internal olefins. The hydrocarbon stream treated in accordance with the present invention may also include hydrocarbons selected from the group consisting of aromatics and paraffins as well as olefins. The aromatic compounds present in the hydrocarbon stream, which may be removed in accordance with the present invention, are selected from the group consisting of benzene, toluene and xylene isomers and mixtures thereof.

The paraffins which may be present in the hydrocarbon stream may be selected from the group consisting of linear paraffins and branched paraffins, and mixtures thereof.

The organosulfur compounds removed from the hydrocarbon stream in accordance with the present invention are selected from the group consisting hydrogen sulfide, mercaptans, sulfides, and disulfides, and mixtures thereof.

In certain applications, the present invention has been found to be particularly useful in eliminating dialkyl sulfides, such as dimethyl sulfide, from hydrocarbon streams which would otherwise have a deleterious effect in a reaction process, for example, in the deactivation of catalytic materials used, for example, in catalytic distillation reaction zones.

In accordance with the present invention, the resultant liquid hydrocarbon stream contains less than about 2 ppm sulfur and preferably less then about 0.2 ppm sulfur. Most preferably, the resultant hydrocarbon stream is substantially devoid of sulfur.

The process of the present invention is performed under conditions including temperatures within the range of about 10° C. to about 100° C. and pressures within the range of about ambient to about 500 psi; preferably the temperatures are within the range of ambient temperatures of 20° C. to about 50° C.

The present invention is particularly suitable for removing organosulfur compounds from hydrocarbons containing olefinic compounds.

As previously discussed, the present invention is directed to the removal of organically-combined sulfur, i.e., organosulfur compounds, from hydrocarbon streams containing organosulfur compounds by subjecting the hydrocarbon stream to appropriate adsorbent materials for a time and under suitable conditions.

For example, in accordance with the present invention, a $C_4$ stream from steam crackers or catalytic crackers for the manufacture of methyl tertiary butyl ether (MTBE), which may contain 15 wt. % isobutylene, 15 wt. % butene-1, 20 wt. % butene-2, 40 wt. % butane, 10 wt. % of $C_3$ and $C_5$, about 400 ppm water, and approximately 1–4 ppm of dimethyl sulfide, is introduced into a water wash column where a counter-current flow of an aqueous solution of suitable N-halogeno compound, such as chloramine-T or chloramine-B, is present. The temperature for this procedure may be within the range of from ambient to 70° C. with ambient to 50° C. being more preferred. The pressure may range from 50 to 500 psi, with 150 to 300 psi being more preferred. The flow rate for the $C_4$ may be from 0.1 to 10 LHSV (Liquid Hourly Space Velocity), with 1 to 3 LHSV being more preferred. The flow rate for water may range from 0.01 to 10 LHSV with 0.02 to 0.6 being more preferred.

Referring to FIG. 1, a counter-current continuous reactive extraction process for sulfur removal in accordance with the present invention is shown. An aqueous solution of a suitable N-halogeno compound is introduced into the extraction tower 1 at the top and flows downwardly. The hydrocarbon feed is introduced at the bottom of the extraction tower or column, and flows upwardly. The extraction column 1 is preferably equipped with proper trays or packing (not shown) to improve mixing efficiency. Sulfur-free hydrocarbons are withdrawn from the top of the column 1 and spent water containing untreated N-halogeno compound and the reaction product of N-halogeno and sulfur is removed from the bottom of the column.

Figure 2:
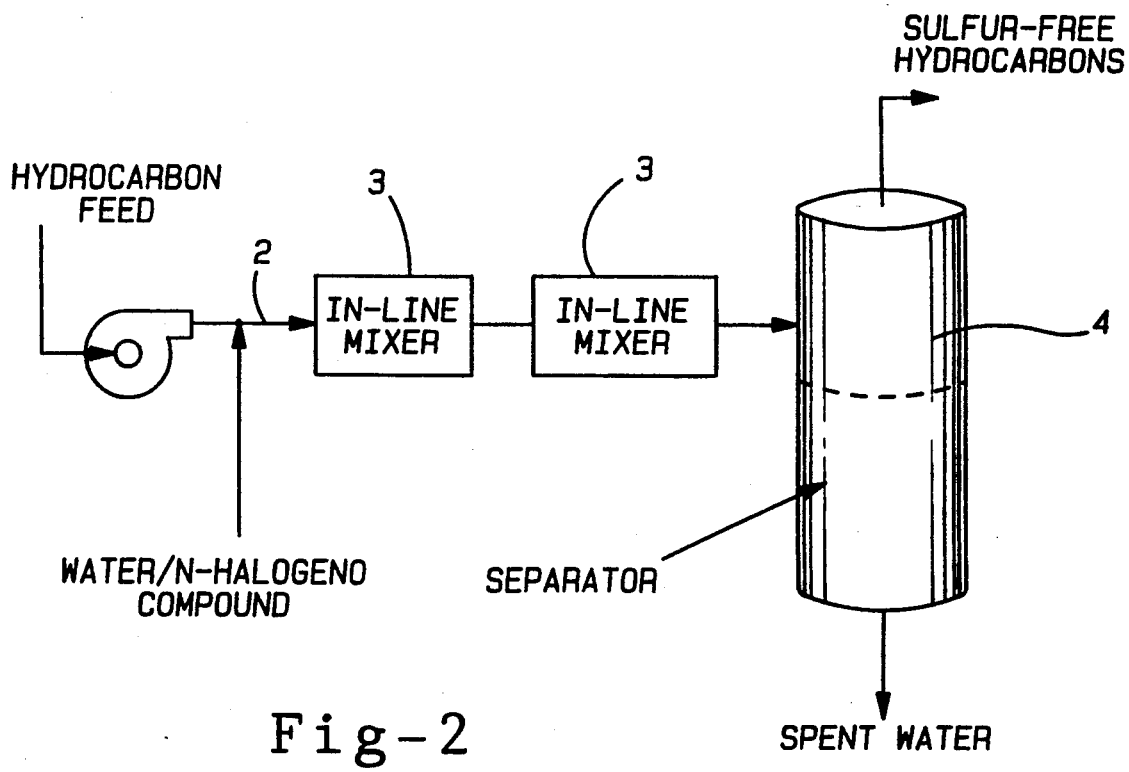
FIG. 2 is an illustration of a con-current continuous reactive extraction process for sulfur removal.

Referring to FIG. 2, a con-current continuous reactive extraction process for sulfur removal in accordance with the present invention is shown. An aqueous solution and hydrocarbon feed are introduced into the same transfer line 2. At least one but preferably a plurality of in-line mixing devices 3, such as orifices or static mixers, are installed further downstream to provide the necessary mixing. The flows are then sent to a separator 4 where sulfur-free hydrocarbons are separated from spent water by phase separation.

Figure 3:
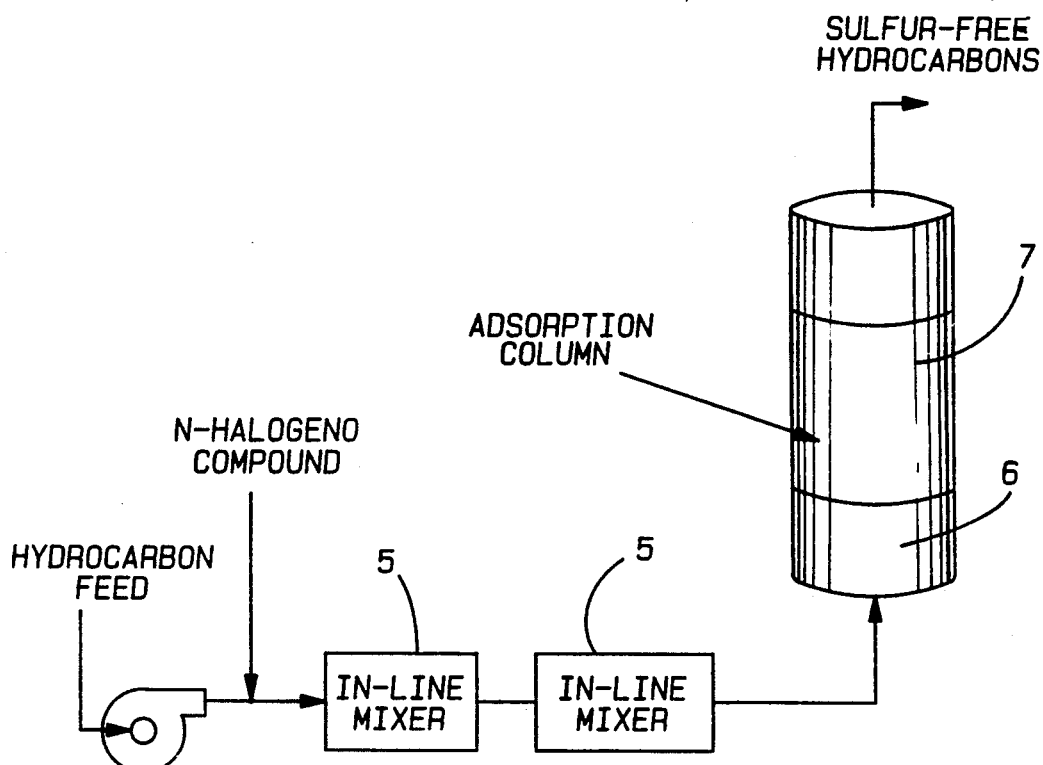
FIG. 3 is an illustration of one of the adsorption processes, referred to herein as Adsorption Process I, of the present invention.

Referring to FIG. 3, an Adsorption Process I, in accordance with the present invention, is shown. A suitable N-halogeno compound is introduced into the hydrocarbon feed. At least one but preferably a plurality of mixing devices 5 are installed downstream of the introduction to provide the necessary mixing. The stream is then sent to an adsorption column 6 with appropriate adsorbent packing 7, in which the reaction product of the N-halogeno compound and sulfur, as well as unreacted N-halogeno compound, are adsorbed by the column. The hydrocarbons leaving the column will be substantially sulfur-free.

Figure 4:
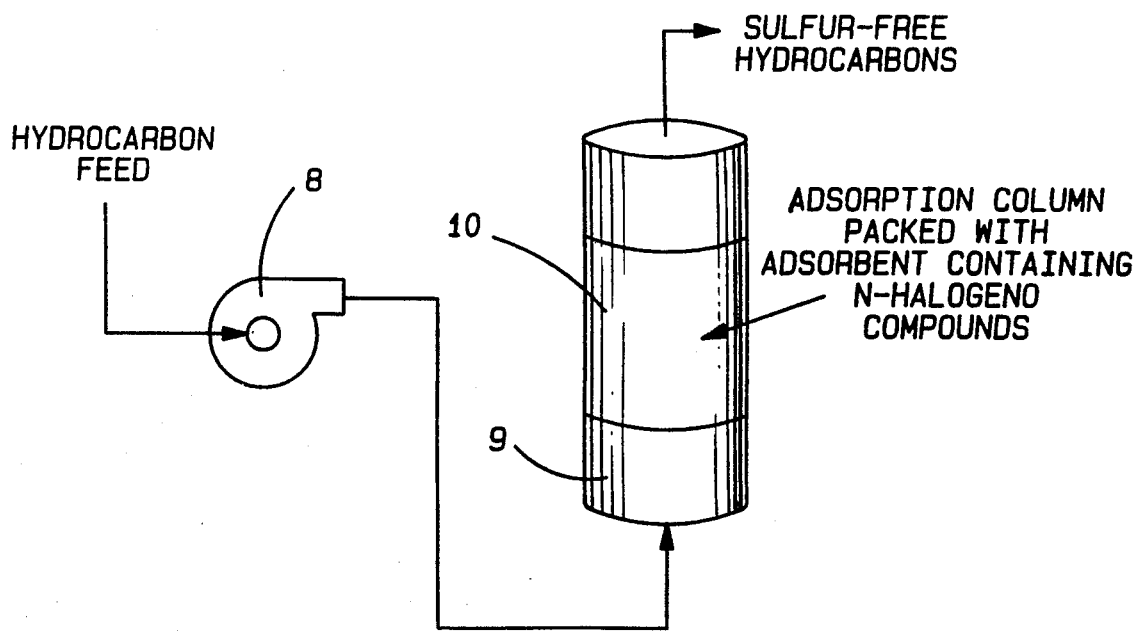
FIG. 4 is an illustration of another adsorption process in accordance with the present invention, referred to herein as Adsorption Process II.

Referring to FIG. 4, an Adsorption Process II, in accordance with the present invention is shown. In this process, the adsorbents used to effect sulfur removal are preloaded with N-halogeno compounds. These adsorbents are prepared by saturating porous supports, such as activated carbons and zeolites, with an aqueous solution of N-halogeno compounds. The N-halogeno compound-loaded adsorbent is then placed as packing 10 in a fixed bed column 9. A hydrocarbon stream is then pumped via pump 8 upwardly through column 9 with adsorbents which are pre-loaded with N-halogeno compounds as packing 10 for sulfur removal. The hydrocarbons leaving the column will be substantially sulfur-free.

The present invention has been found to be particularly useful in removing organosulfur compounds present in the hydrocarbon stream in relatively small amounts.

EXAMPLES

The following non-limiting examples are given by way of illustration of the present invention.

EXAMPLE I

Reactive Extraction

In this Example, an aqueous solution of 0.6 wt. % chloramine-T/99.4 wt. % water, and 0.7 wt. % chloramine-B/99.3 wt. % were used to extract dimethyl sulfide (DMS), ethyl methyl sulfide (EMS), diethyl sulfide (DES), ethyl mercaptan (ETSH), or dimethyl disulfide (DMDS) from a number of hydrocarbon streams, as identified below in Table 1 as "hydrocarbon phase composition."

The chloramine solution and hydrocarbon stream were placed in a sealed bottle and mixed with a stirrer at 21° C. and atmospheric pressure for 21 hours.

The separation of N-halogeno compounds and hydrocarbons was easily achieved inasmuch as the two solutions were immiscible, merely by stopping the stirrer. After the extraction, the upper hydrocarbon phase was sampled for sulfur analysis. The results are presented below in Table 1.

TABLE 1

| | Reactive Extraction | | |
|---|---|---|---|
| Hydrocarbon Phase Composition | Extraction Phase Composition | Wt. Ratio | Sulfur in Hydrocarbon after Extraction |
| 85% $C_7$ 15% Butadiene 25 ppm DMS | 99.4% Water 0.6% CT | 69:1 | <1 ppm |
| 85% $C_7$ 15% Butadiene 25 ppm DMS | 99.3% Water 0.7% CB | 65:1 | <1 ppm |

TABLE 1-continued

| Hydrocarbon Phase Composition | Reactive Extraction Extraction Phase Composition | Wt. Ratio | Sulfur in Hydrocarbon after Extraction |
|---|---|---|---|
| 85% C$_7$ 15% Butadiene 25 ppm EMS | 99.4% Water 0.6% CT | 75:1 | <1 ppm |
| 85% C$_7$ 15% Butadiene 25 ppm DES | 99.4% Water 0.6% CT | 55:1 | <1 ppm |
| 85% C$_7$ 15% Butadiene 25 ppm DMDS | 99.4% Water 0.6% CT | 15:1 | <1 ppm |
| 85% C$_7$ 15% Butadiene 25 ppm EtSH | 99.4% Water 0.6% CT | 67:1 | <1 ppm |
| 40% Butane 60% Butenes 15 ppm DMS 13 ppm ETSH | 99.4% Water 0.6% CT | 52:1 | <1 ppm |

In view of the foregoing, it appears that N-halogeno compounds could reduce sulfur concentrations to below 1 ppm even when butadiene is present.

EXAMPLE 2

Reaction Adsorption Process

Experiments were conducted to show the effectiveness of reactive adsorption.

Experiment A was a reference test conducted as follows: a feed solution of 10 ppm DMS, 15 wt. % isobutylene, and 85 wt. % n-heptane was pumped through a 5 cc stainless steel column packed with sodium X-Zeolite at 20° C., 300 psig and 2 Liquid Hourly Space Velocity (LHSV). The column effluent was analyzed to determine DMS break-through and the adsorption capacity of Na-X Zeolite.

In Experiments B and C, a stoichiometric amount of 37 ppm chloramine-T and 35 ppm chloramine-B were added to the feed solutions, respectively. In other respects, the test, including the test conditions, was unchanged.

Experiments B and C were compared to Experiment A (the control) for the effectiveness of N-halogeno compounds in the removal of sulfur contaminants from hydrocarbon streams.

The feed compositions and the test results are tabulated below in Table 2.

TABLE 2

| Reactive Adsorption I | |
|---|---|
| Feed Composition | Na-X Capacity |
| 85% C$_7$ 15% Isobutylene 10 ppm DMS | 0.15% |
| 85% C$_7$ 15% Isobutylene 10 ppm DMS 37 ppm CT 400 ppm Water | >0.72% |
| 85% C$_7$ 15% Isobutylene 10 ppm DMS 35 ppm CB 400 ppm Water | >0.72% |

In view of the foregoing, it appears that adding N-halogeno compounds to hydrocarbons more than quadrupled the DMS capacity of Na-X zeolite.

In addition, tests have been run which have generated data to indicate that N-halogeno compounds are capable of removing mercaptans, sulfides and disulfides even from streams containing high levels of olefins.

For this purpose, the following examples were run:

EXAMPLE 3

This example demonstrates a continuous reactive extraction process for dimethyl-sulfide removal from a hydrocarbon stream with high olefin concentration. The stream was composed of 15 wt. % iso-butylene, 15 wt. % butene-1, 20 wt. % butene-2, about 40 wt. % butanes, 10 wt. of C$_3$ and C$_5$ compounds, approximately 400 ppm water, and 9 ppm dimethyl sulfide. A water solution containing 1000 ppm chloramine-T was used as extraction agent. The extraction was conducted inside a ¼"×3" glass tubing in a vertical position at ambient temperature and 120 psi. Water/chloramine-T was pumped into the bottom of the tubing at a rate of 0.14 g/min. After the tubing was completely filled with water/chloramine-T, the hydrocarbon feed was introduced into the tubing at a rate of 0.7 g/min. through a nozzle located in the bottom of the tubing. The flow leaving the top of the tubing was sent to a separator where feed and water/chloramine-T were separated by phase separation. The contact time inside the glass tubing was on the order of 5 to 10 seconds. Samples taken from the treated hydrocarbon showed a DMS concentration of less than 0.2 ppm.

The preferred embodiments for purposes of the present invention, i.e., effecting the removal of sulfur contaminants from hydrocarbons using N-halogeno compounds include a reactive extraction process, and two reactive adsorption processes.

The preferred reactive extraction process is accomplished using liquid/liquid extraction techniques. In accordance with the present invention, it has been discovered that some N-halogeno compounds, e.g., those identified herein, and the reaction products of these N-halogeno compounds and sulfur compounds are more soluble in water, than in paraffins, olefins or aromatics. Thus, in the liquid/liquid reactive extraction processes, an aqueous solution of N-halogeno compounds is prepared and permitted to react with the sulfur compounds upon exposure to the sulfur compounds which are present in the hydrocarbon stream and the reaction products are then extracted from the hydrocarbon phase to the aqueous phase using one of these reactive extraction techniques.

As an alternative, however, a reactive adsorption process, hereinafter designated as Adsorption Process I or Adsorption Process II, may be used.

The Adsorption Process I involves injecting a stoichiometric amount of N-halogeno compounds into the hydrocarbon stream containing the sulfur contaminants, and then passing the hydrocarbon stream through an adsorbent column to adsorb the N-halogeno-sulfur compounds and any unreacted N-halogeno compounds.

In the Adsorption Process II, sulfur removal is accomplished using adsorbents which are pre-loaded with N-halogeno compounds. In this embodiment, adsorbents are prepared by saturating pore supports, such as activated carbon and zeolites with N-halogeno compounds. The N-halogeno-loaded adsorbent is then placed in a fixed-bed for sulfur removal and the hydrocarbon stream containing sulfur contaminants is passed therethrough.

It will also be appreciated by those of ordinary skill in the art that, while the present invention has been described herein by reference to particular means, methods and materials, the scope of the present invention is not limited thereby and extends to any and all other means, methods and materials suitable for practice of the present invention. Therefore, although the present invention has been described with reference to particular means, materials and embodiments, from the foregoing description one skilled in the art can easily ascertain the essential characteristics of the present invention, and various changes and modifications may be made to various usages and conditions, without departing from the spirit and scope of the invention as described in the claims that follow.

What is claimed is:

1. A process for the removal of organosulfur compounds from a liquid hydrocarbon stream containing organosulfur compounds, said process comprising:
exposing a liquid hydrocarbon stream comprising an organosulfur compound to a material comprising a N-halogeno compound under conditions and time effective to permit said organosulfur compound to react with said N-halogeno compounds to result in a resultant liquid hydrocarbon stream which is substantially devoid of sulfur.

2. The process as defined by claim 1, wherein said resultant liquid hydrocarbon stream contains less than about 0.2 ppm sulfur.

3. The process as defined by claim 1, wherein said exposing is accomplished by a technique selected from the group consisting of a liquid-liquid reactive extraction process, and a reactive adsorption process.

4. The process as defined by claim 3, wherein said N-halogeno compounds are selected from the group of halogen-compounds having a general formula selected from the following group of formulae:

$$R_1SO_2NXM \qquad (I)$$

wherein $R_1$ is a member selected from the group consisting of Ph, PhCH$_2$, p—CH$_3$C$_6$H$_4$, p—ClC$_6$H$_4$, p—BrC$_6$H$_4$, p—NO$_2$C$_6$H$_4$, p—CH$_3$CONHC$_6$H$_4$, p—NH$_2$C$_6$H$_4$, p—PhN=NC$_6$H$_4$, 2-Thienyl, and (CH$_3$)$_m$(CH$_2$)$_n$, where m and n are integers equal to or greater than zero; X is a radical selected from the group consisting of chlorine, bromine, and iodine radicals; and M is a radical selected from the group consisting of hydrogen, lithium, sodium, and potassium radicals;

$$R_2CONXM \qquad (II)$$

wherein $R_2$ is a member selected from the group consisting of CH$_2$Cl, CHCl$_2$, CHBr$_2$, NH$_2$, Ph, p—CH$_3$OC$_6$H$_4$, (CH$_3$)$_m$(CH$_2$)$_n$, and (CH$_3$)$_m$(CH$_2$)$_n$O, wherein m and n are integers equal to or greater than zero; X is a radical selected from the group consisting of chlorine, bromine, and iodine radicals; and M is a radical selected from the group consisting of hydrogen, lithium, sodium, and potassium radicals;

$$R_4N=C\begin{subarray}{l}NXM\\R_3\end{subarray} \qquad (III)$$

wherein $R_3$ is a member selected from the group consisting of CH$_3$ and Ph; and wherein $R_4$ is a member selected from the group consisting of H, NH$_2$, N(CH$_3$)$_2$, (CH$_2$)$_3$, Ph, PhCl$_2$, p—CH$_3$C$_6$H$_4$, o—CH$_3$C$_6$H$_4$, p—ClC$_6$H$_4$, o—ClC$_6$H$_4$, and 2-Pyridyl; X is a radical selected from the group consisting of chlorine, bromine, and iodine radicals; and M is a radical selected from the group consisting of hydrogen, lithium, sodium, and potassium radicals;

$$C_4H_4O_2NX \qquad (IV)$$

wherein X is a radical selected from the group consisting of chlorine, bromine, and iodine radicals.

5. The process as defined by claim 4, wherein the liquid of the reactive extraction process is an aqueous liquid.

6. The process as defined by claim 5, wherein said material comprising N-halogeno compounds is an aqueous solution of water-soluble N-halogeno compounds.

7. The process as defined by claim 6, wherein said N-halogeno compounds are selected from the group consisting of N-halogeno-N-metalloarylsulfonamidates and N-halogeno-N-metalloalkylsulfonamidates.

8. The process as defined by claim 4, wherein said reactive adsorption process comprises injecting a stoichiometric amount of N-halogeno compounds into said hydrocarbon stream, and then passing said hydrocarbon stream containing said N-halogeno compounds through an adsorbent column to adsorb N-halogeno-sulfur compounds and unreacted N-halogeno compounds.

9. The process as defined by claim 8, wherein said adsorbent is selected from the group consisting of activated carbon, clay, alumina, silica gel, and molecular sieve material.

10. The process as defined by claim 4, wherein said material comprising N-halogeno compounds is an adsorbent which has been pre-loaded with said N-halogeno compounds.

11. The process as defined by claim 10, wherein said adsorbent pre-loaded with said N-halogeno compounds is provided by saturating a porous support with said N-halogeno compounds to result in a N-halogeno compound-loaded adsorbent; and then supplying said N-halogeno compound-loaded adsorbent in a fixed-bed column; and subsequently passing said hydrocarbon stream comprising an organosulfur compound through said fixed-bed column containing said N-halogeno compound-loaded adsorbent.

12. The process as defined by claim 11, wherein said adsorbent and said porous support is a material selected from a group consisting of activated carbon, clay, alumina, silica gel and molecular sieve material.

13. The process as defined by claim 12, wherein said molecular sieve material is selected from the group of highly crystalline molecular sieve materials having a pore size within the range of more than 5 Angstrom units to about 15 Angstrom units.

14. The process as defined by claim 13, wherein said zeolites are selected from the group consisting of zeolite X, Y, beta, and mordenite.

15. The process as defined by claim 14, wherein said zeolites are selected from the group of cation-exchanged zeolites.

16. The process as defined by claim 15, wherein the cations in said cation-exchanged zeolites are selected from the group consisting of alkali metals and alkaline earth metals.

17. The process as defined by claim 3, wherein said hydrocarbon stream comprises hydrocarbons selected from the group consisting of aromatics, paraffins and olefins.

18. The process as defined by claim 17, wherein said olefinic compounds are selected from the group consisting of mono-olefins, polyolefins, linear olefins, branched olefins, alpha olefins, and internal olefins.

19. The process as defined by claim 18, wherein said conditions comprise temperatures within the range of about 10° C. to about 100° C., and pressures within the range of about ambient to about 500 psi.

20. The process as defined by claim 19, wherein said temperatures are within the range of ambient temperatures of 20° C. to about 50° C.

21. A process for the removal of organosulfur compounds from a liquid hydrocarbon stream containing organosulfur compounds, said process comprising:

exposing a liquid hydrocarbon stream comprising an organosulfur compound to an adsorbent which has been pre-loaded with N-halogeno compounds by saturating a porous support molecular sieve material selected from the group consisting of highly crystalline molecular sieve materials having a pore size within the range of more than 5 Angstrom units to about 15 Angstrom units with said N-halogeno compounds to result in a N-halogeno compound-loaded adsorbent; and then supplying said N-halogeno compound-loaded adsorbent in a fixed-bed column; and subsequently passing said hydrocarbon stream comprising an organosulfur compound through said fixed-bed column containing said N-halogeno compound-loaded adsorbent, wherein said N-halogeno compound is selected from the group of halogen-compounds having a general formula selected from the following group of formulae:

$$R_1SO_2NXM \quad (I)$$

wherein $R_1$ is a member selected from the group consisting of Ph, PhCH$_2$, p—CH$_3$C$_6$H$_4$, p—ClC$_6$H$_4$, p—BrC$_6$H$_4$, p—NO$_2$C$_6$H$_4$, p—CH$_3$CONHC$_6$H$_4$, p—NH$_2$C$_6$H$_4$, p—PhN=NC$_6$H$_4$, 2-Thienyl, and (CH$_3$)$_m$(CH$_2$)$_n$, where m and n are integers equal to or greater than zero; X is a radical selected from the group consisting of chlorine, bromine, and iodine radicals; and M is a radical selected from the group consisting of hydrogen, lithium, sodium, and potassium radicals;

$$R_2CONXM \quad (II)$$

wherein $R_2$ is a member selected from the group consisting of CH$_2$Cl, CHCl$_2$, CHBr$_2$, NH$_2$, Ph, p—CH$_3$OC$_6$H$_4$, (CH$_3$)$_m$(CH$_2$)$_n$, and (CH$_3$)$_m$(CH$_2$)$_n$O, wherein m and n are integers equal to or greater than zero, X is a radical selected from the group consisting of chlorine, bromine, and idozine radicals; and M is a radical selected from the group consisting of hydrogen, lithium, sodium, and potassium radicals;

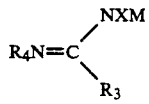

wherein $R_3$ is a member selected from the group consisting of CH$_3$ and Ph, and wherein $R_4$ is a member selected from the group consisting of H, NH$_2$, N(CH$_3$)$_2$, (CH$_2$)$_3$, Ph, PhCl$_2$, p—CH$_3$C$_6$H$_4$, o—CH$_3$C$_6$H$_4$, p—ClC$_6$H$_4$, o—ClC$_6$H$_4$, and 2-Pyridyl; X is a radical selected from the group consisting of chlorine, bromine, and iodine radicals; and M is a radical selected from the group consisting of hydrogen, lithium, sodium, and potassium radicals; and $$C_4H_4O_2NX \quad (IV)$$

wherein X is a radical selected from the group consisting of chlorine, bromine, and iodine radicals, said exposing comprising using a technique selected from the group consisting of a liquid-liquid reactive extraction process and a reactive adsorption process under conditions and time effective to permit said organosulfur compound to react with said N-halogeno compounds to result in a resultant liquid hydrocarbon stream which is substantially devoid of sulfur.

22. The process as defined by claim 21, wherein said zeolites are selected from the group consisting of zeolite, X, Y, beta, and mordenite.

23. The process as defined by claim 22, wherein said zeolites are selected from the group of cation-exchanged zeolites.

24. The process as defined by claim 23, wherein the cations in said cation-exchanged zeolites are selected from the group consisting of alkali metals and alkaline earth metals.

* * * * *